United States Patent
Naud et al.

(10) Patent No.: US 10,501,462 B2
(45) Date of Patent: Dec. 10, 2019

(54) PYRROLO[3,2-C]PYRIDINE-6-AMINO DERIVATIVES

(71) Applicant: CANCER RESEARCH TECHNOLOGY LIMITED, London (GB)

(72) Inventors: Sebastien Gaston Andre Naud, London (GB); Julian Blagg, London (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 16/064,297

(22) PCT Filed: Dec. 20, 2016

(86) PCT No.: PCT/GB2016/054003
§ 371 (c)(1),
(2) Date: Jun. 20, 2018

(87) PCT Pub. No.: WO2017/109476
PCT Pub. Date: Jun. 29, 2017

(65) Prior Publication Data
US 2019/0002462 A1   Jan. 3, 2019

(30) Foreign Application Priority Data
Dec. 21, 2015 (GB) .................... 1522532.9

(51) Int. Cl.
*C07D 471/04* (2006.01)
*A61P 35/00* (2006.01)
(52) U.S. Cl.
CPC ............ *C07D 471/04* (2013.01); *A61P 35/00* (2018.01)
(58) Field of Classification Search
CPC .................................................. C07D 471/04
See application file for complete search history.

(56) References Cited

U.S. PATENT DOCUMENTS 9,371,319 B2 * 6/2016 Bavetsias ............. C07D 471/04

FOREIGN PATENT DOCUMENTS

WO  WO-2012/123745 A1   9/2012
WO  WO-2014037750 A1 * 3/2014 ........... C07D 401/14

OTHER PUBLICATIONS

Kusakabe "A unique hinge binder of extremely selective aminopyridine-based Mps1 (TTK) kinase inhibitors with cellular activity" Bioorganic & Medicinal Chemistry 23 (2015) 2247-2260.*
Henriques "Mitosis inhibitors in anticancer therapy: When blocking the exit becomes a Solution" Cancer Letters 440-441 (2019) 64-81.*
Xie "Mps1/TTK: a novel target and biomarker for cancer" Journal of Drug Targeting, 2017 vol. 25, No. 2, 112-118.*
Jemaa "Characterization of novel MPS1 inhibitors with preclinical anticancer activity" Cell Death and Differentiation (2013) 20, 1532-1545.*
Kumar "Lead optimization of purine based orally bioavailable Mps1 (TTK) inhibitors" Bioorganic & Medicinal Chemistry Letters 22 (2012) 4377-4385.*
International Search Report and Written Opinion for International Application No. PCT/GB2016/054003 dated Mar. 10, 2017.
Naud et al., "Structure-based Design of Orally Bioavailable 1H-pyrrolo[3,2-c]pyridine Inhibitors of Mitotic Kinase Monopolar Spindle 1 (MPS1)," Journal of Medicinal Chemistry, 56: 10045-10065 (2013).
UK Search Report for GB Application No. GB1522532.9 dated Oct. 11, 2016.

* cited by examiner

*Primary Examiner* — David K O'Dell
(74) *Attorney, Agent, or Firm* — Foley Hoag LLP; David P. Halstead; Lucas P. Watkins

(57) ABSTRACT

The present invention relates to novel pyrrolo[3,2-c]pyridine-6-amino derivatives that inhibit the spindle checkpoint function of Monospindle 1 (Mps1—also known as TTK) kinases. In particular, the present invention relates to isopropyl 6-(2-methoxy-4-(1-methyl-1H-1,2,3-triazol-5-yl)phenylamino)-2-(1-methyl-1H-pyrazol-4-yl)-1H-pyrrolo[3,2-c]pyridine-1-carboxylate and isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate and their use as therapeutic agents for the treatment and/or prevention of proliferative diseases, such as cancer. The present invention also relates to processes for the preparation of these compounds and to pharmaceutical compositions comprising them.

10 Claims, No Drawings

PYRROLO[3,2-C]PYRIDINE-6-AMINO DERIVATIVES

CROSS-REFERENCE TO RELATED APPLICATIONS

This application is a § 371 national stage application based on Patent Cooperation Treaty Application serial number PCT/GB2016/054003, filed Dec. 20, 2016; which claims the benefit of priority to United Kingdom Patent Application No. GB 1522532.9, filed Dec. 21, 2015. The Patent Cooperation Treaty Application is hereby fully incorporated by reference herein.

INTRODUCTION

The present invention relates to certain novel pyrrolo[3,2-c]pyridine-6-amino derivatives that function as inhibitors of monopolar spindle 1 (Mps1—also known as TTK) kinase activity. In particular, the present invention relates to the novel pyrrolo[3,2-c]pyridine-6-amino derivatives per se, their use in the treatment and/or prevention of proliferative diseases (such as, for example, cancer), processes for the preparation of these derivatives, and pharmaceutical compositions comprising them.

BACKGROUND OF THE INVENTION

Cancer is caused by uncontrolled and unregulated cellular proliferation. Precisely what causes a cell to become malignant and proliferate in an uncontrolled and unregulated manner has been the focus of intense research over recent decades. This research has led to the targeting of surveillance mechanisms, such as those responsible for regulating the cell cycle, with anticancer agents.

The main role of the cell cycle is to enable error-free DNA replication, chromosome segregation and cytokinesis. Surveillance mechanisms, the so-called checkpoint pathways, monitor passage through mitosis at several stages. One of the best characterised is the spindle assembly checkpoint that prevents anaphase onset until the appropriate tension and attachment across kinetochores is achieved (HARDWICK KG, 1998, "The spindle checkpoint", *Trends Genet* 14, 1-4). The majority of proteins involved in the checkpoint exert their functions through protein binding interactions with the involvement of only a small number of kinases (MUSACCHIO A et al, 2007, "The spindle-assembly checkpoint in space and time", *Nature Reviews, Molecular and Cell Biology*, 8, 379-393). A mitotic checkpoint complex (MCC) that contains three checkpoint proteins (Mad2, BubR1/Mad3, Bub3) and the APC/C co-factor, CDC20, concentrates at the kinetochores and acts as a spindle checkpoint effector. Other core proteins required to amplify the checkpoint signal include Mad1 and the kinases Bub1, Mps1 (also known as TTK) and Aurora-B (MUSACCHIO, referenced above).

One of the first components of the spindle assembly checkpoint signal, identified by a genetic screen in budding yeast, was dubbed Mps1 (monopolar spindle 1) for the monopolar spindles produced by Mps1 mutant cells (WEISS E, 1996, "The *Saccharomyces cerevisiae* spindle pole body duplication gene MPS1 is part of a mitotic checkpoint", *J Cell Biol* 132, 111-123), however, it still remains one of the least studied checkpoint components in higher eukaryotes. Subsequently, the Mps1 gene was shown to encode an essential dual-specificity kinase (LAUZE et al, 1995, "Yeast spindle pole body duplication gene MPS1 encodes an essential dual specificity protein kinase", *EMBO J* 14, 1655-1663 and also POCH et al, 1994, "RPK1, an essential yeast protein kinase involved in the regulation of the onset of mitosis, shows homology to mammalian dual-specificity kinases", *Mol Gen Genet* 243, 641-653) conserved from yeast to humans (MILLS et al, 1992, "Expression of TTK, a novel human protein kinase, is associated with cell proliferation", *J Biol Chem* 267, 16000-16006). Mps1 activity peaks at the $G_2$/M transition and is enhanced upon activation of the spindle checkpoint with nocodazole (STUCKE et al, 2002, "Human Mps1 kinase is required for the spindle assembly checkpoint but not for centrosome duplication", *EMBO J* 21, 1723-1732 and also LIU et al, 2003, "Human MPS1 kinase is required for mitotic arrest induced by the loss of CENP-E from kinetochores", *Mol Biol Cell* 14, 1638-1651). The autophosphorylation of Mps1 at Thr676 in the activation loop has been identified and is essential for Mps1 function (MATTISON et al, 2007, "Mps1 activation loop autophosphorylation enhances kinase activity", *J Biol Chem* 282, 30553-30561).

Given the importance of Mps1 in spindle checkpoint activation, the development of Mps1 inhibitors would be an asset, not only as a tool to further investigate its cell cycle-related functions, but also as a form of anticancer treatment. The first generation inhibitors of Mps1 have been described. Cincreasin, caused chromosome mis-segregation and death in yeast cells (DORER et al, 2005, "A small-molecule inhibitor of Mps1 blocks the spindle-checkpoint response to a lack of tension on mitotic chromosomes", *Curr Biol* 15, 1070-1076) and SP600125, a JNK (c-Jun amino-terminal kinase) inhibitor, also disrupts spindle checkpoint function in a JNK-independent manner via the inhibition of Mps1 (SCHMIDT et al, 2005, "Ablation of the spindle assembly checkpoint by a compound targeting Mps1", *EMBO Rep* 6, 866-872). Recently, three small molecule inhibitors of Mps1 were identified (KWIATOWSKI et al, 2010, "Small-molecule kinase inhibitors provide insight into Mps1 cell cycle function", *Nat Chem Biol* 6, 359-368; HEWITT et al, 2010, "Sustained Mps1 activity is required in mitosis to recruit O-Mad2 to the Mad1-C-Mad2 core complex", *J Cell Biol* 190, 25-34; and SANTAGUIDA et al, 2010, "Dissecting the role of MPS1 in chromosome biorientation and the spindle checkpoint through the small molecule inhibitor reversine", *J Cell Biol* 190, 73-87). Chemical inhibition of Mps1 induced premature mitotic exit, gross aneuploidy and death to human cancer cell lines (KWIATOWSKI above). Mps1 inhibitors AZ3146 and reversine, severely impaired recruitment of Mad1, Mad2 and CENP-E to kinetochores (HEWITT, and SANTAGUIDA above).

Dysregulation of the mitotic checkpoint is recognised as a feature of the malignant transformation process. Mitotic checkpoint dysfunction in tumors provides an opportunity for developing a therapeutic strategy using small molecules. This is based on the proposition that pharmacologic disruption of an already compromised mitotic checkpoint may selectively sensitize tumors. This observation has led to the hypothesis that inhibition of Mps1 may be of therapeutic benefit.

WO 2012/123745 (Cancer Research Technology Limited) describes a series of compounds that function as inhibitors of Mps1 activity. The compounds described in WO2012/123745 all have the general structural formula shown below:

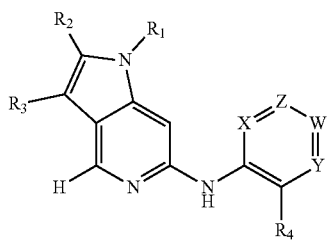

The groups $R_1$, $R_2$, $R_3$, $R_4$, w, x, y and z are all defined in WO2012/123745.

The compounds described in WO2012/123745 are potent Mps1 inhibitors. However, there remains a need for further compounds that are potent Mps1 inhibitors and which also possess one or more additional advantageous pharmaceutical properties. In particular, there is a need for compounds that are potent inhibitors of Mps1 activity, but which also possess low toxicity; good stability to human liver microsomes, and a good PK profile (in particular, low levels of clearance).

The compounds of the present invention were devised with the foregoing in mind.

SUMMARY OF THE INVENTION

In one aspect, the present invention provides a compound selected from:

isopropyl 6-(2-methoxy-4-(1-methyl-1H-1,2,3-triazol-5-yl)phenylamino)-2-(1-methyl-1H-pyrazol-4-yl)-1H-pyrrolo[3,2-c]pyridine-1-carboxylate; or isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate;

or a pharmaceutically acceptable salt or solvate thereof.

WO 2012/123745 discloses the particular compounds shown in Table 1 below:

| Example No. in WO2012/123745 | Name/Structure |
| --- | --- |
| 18 | tert-Butyl 6-(2-chloro-4-(4-methyl-4H-1,2,4-triaozl-3-yl)phenylamino)-2-(1-methyl-1H-pyrazol-4-yl)-1H-pyrrolo[3,2-c]pyridine-1-carboxylate 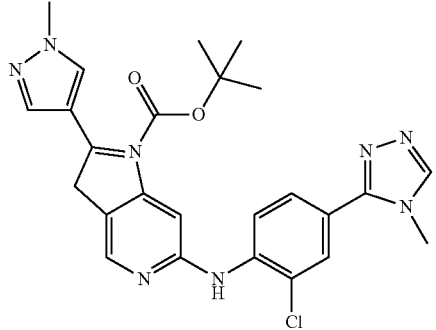 |
| 22 | tert-Butyl 6-(2-chloro-4-(1-methyl-1H-imidazol-2-yl)phenylamino)-2-(1-methyl-1H-pyrazol-4-yl)-1H-pyrrolo[3,2-c]pyridine-1-carboxylate 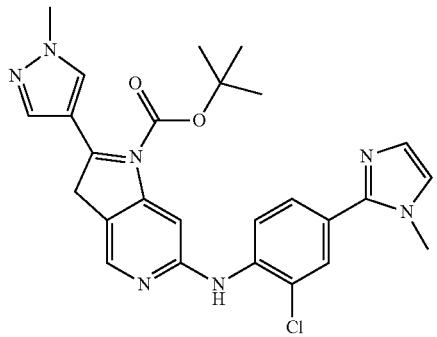 |

| Example No. in WO2012/123745 | Name/Structure |
|---|---|
| 44 | tert-Butyl 6-(2-chloro-4-(1-methyl-1H-pyrazol-5-yl)phenylamino)-2-(1-methyl-1H-pyrazol-4-yl)-1H-pyrrolo[3,2-c]pyridine-1-carboxylate 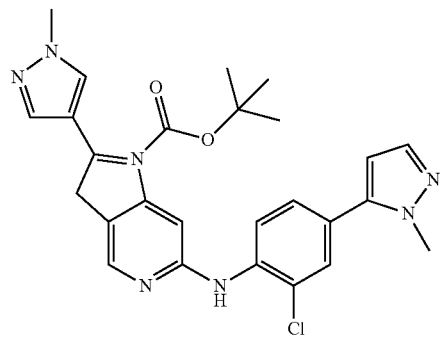 |
| 68 | Isopropyl 6-(4-(1,2-dimethyl-1H-imidazol-5-yl)-2-methoxyphenylamino)-2-(1-methyl-1H-pyrazol-4-yl)-1H-pyrrolo[3,2-c]pyridine-1-carboxylate 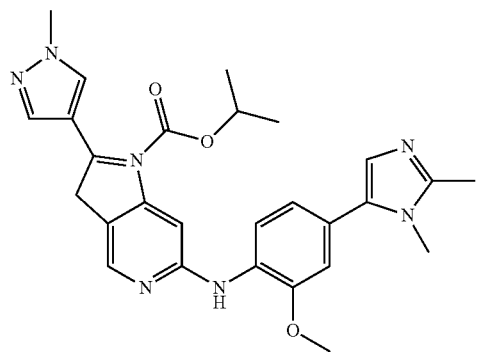 |
| 79 | Isopropyl 6-(2-chloro-4-(1-methyl-1H-imidazol-5-yl)phenylamino)-2-(1-methyl-1H-pyrazol-4-yl)-1H-pyrrolo[3,2-c]pyridine-1-carboxylate 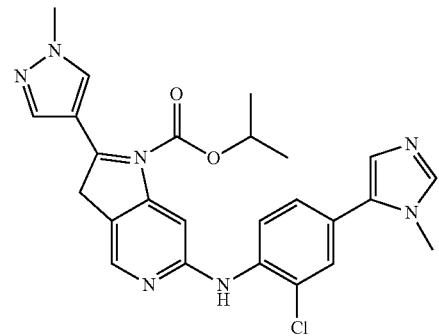 |

-continued

| Example No. in WO2012/123745 | Name/Structure |
|---|---|
| 102 | Isopropyl 6-(2-methoxy-4-(1-methyl-1H-pyrazol-4-yl)phenylamino)-2-(1-methyl-1H-pyrazol-4-yl)-1H-pyrrolo[3,2-c]pyridine-1-carboxylate 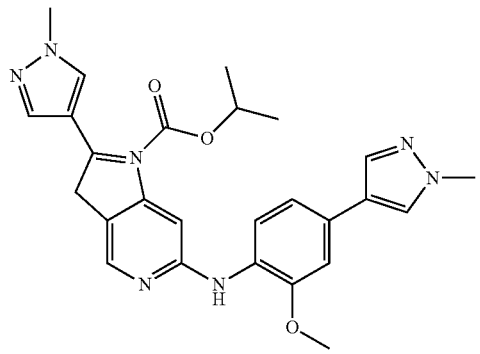 |
| 103 | Isopropyl 6-(4-(1,3-dimethyl-1H-pyrazol-4-yl)-2-methoxyphenylamino)-2-(1-methyl-1H-pyrazol-4-yl)-1H-pyrrolo[3,2-c]pyridine-1-carboxylate 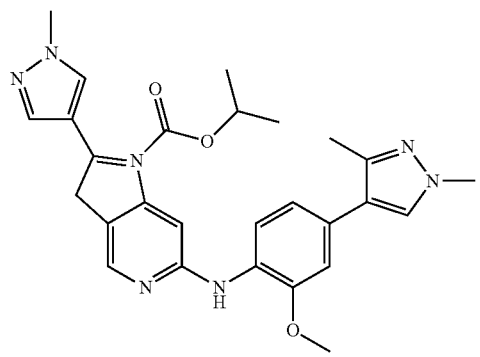 |

In comparison with the above-identified compounds described in WO2012/123745, the compounds of the present invention are potent Mps1 inhibitors that surprisingly possess a number of additional advantageous properties, including:

(i) $GI_{50}$ values of 0.15 micromolar or less in the MTT HCT116 toxicity assay described Example 3 herein;

(ii) good microsomal stability (as evidenced by a value of less than 30% degradation of the compound after 30 minutes incubation in the human liver microsome assay described in Example 3 herein); and (iii) improved pharmacokinetic profiles (in particular low levels of clearance, as evidenced by a clearance value of less than 3.5 mL/min/Kg in the mouse PK study described in Example 3 herein).

Data is set out in Example 3 herein to demonstrate these advantageous properties for the compounds of the present invention. Comparative data is also provided for the above-identified compounds from WO2012/123745.

In another aspect, the present invention provides a pharmaceutical composition comprising a compound as defined herein, or a pharmaceutically acceptable salt or solvate thereof, and a pharmaceutically acceptable excipient (e.g. a pharmaceutically acceptable diluent or carrier).

In another aspect, the present invention provides a compound, or a pharmaceutically acceptable salt or solvate thereof, as defined herein, or a pharmaceutical composition as defined herein, for use in the treatment of a proliferative condition.

In another aspect, the present invention provides a compound, or a pharmaceutically acceptable salt or solvate thereof, as defined herein, or a pharmaceutical composition as defined herein, for use in the treatment of cancer. In a particular embodiment, the cancer is a human cancer.

In another aspect, the present invention provides a compound, or a pharmaceutically acceptable salt or solvate thereof, as defined herein, or a pharmaceutical composition as defined herein, for use in the production of a Mps1 kinase inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of an Mps1 kinase inhibitory effect.

In another aspect, the present invention provides a method of inhibiting Mps1 kinase in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

In another aspect, the present invention provides a compound, or a pharmaceutically acceptable salt or solvate thereof, or a pharmaceutical composition as defined herein, for use in therapy.

The present invention further provides a method of synthesising a compound, or a pharmaceutically acceptable salt or solvate thereof, as defined herein.

In another aspect, the present invention provides a compound, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The phrase "compound of the invention" means those compounds which are disclosed herein, both generically and specifically.

The Compounds of the Invention

In one aspect, the present invention provides a compound selected from one of the following:
isopropyl 6-(2-methoxy-4-(1-methyl-1H-1,2,3-triazol-5-yl) phenylamino)-2-(1-methyl-1H-pyrazol-4-yl)-1H-pyrrolo [3,2-c]pyridine-1-carboxylate; or
isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate;
or a pharmaceutically acceptable salt or solvate thereof.

The compounds of the invention may be represented by the following structural formula I:

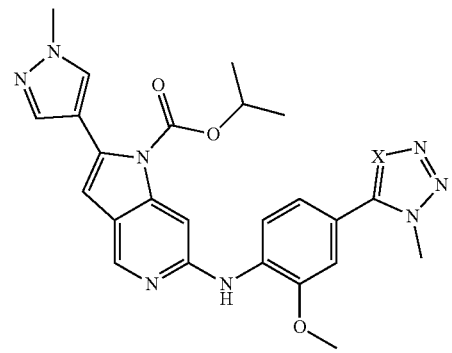

wherein x is N or CH;
or a pharmaceutically acceptable salt or solvate thereof.

In an embodiment x is CH, i.e. the compound is isopropyl 6-(2-methoxy-4-(1-methyl-1H-1,2,3-triazol-5-yl)phenylamino)-2-(1-methyl-1H-pyrazol-4-yl)-1H-pyrrolo[3,2-c]pyridine-1-carboxylate, or a pharmaceutically acceptable salt or solvate thereof.

In another embodiment x is N, i.e. the compound is isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate, or a pharmaceutically acceptable salt or solvate thereof.

A suitable pharmaceutically acceptable salt of a compound of the invention is, for example, an acid-addition salt of a compound of the invention, for example, an acid-addition salt with, for example, an inorganic or organic acid, for example hydrochloric, hydrobromic, sulfuric, phosphoric, trifluoroacetic, formic, citric or maleic acid.

The present invention also encompasses compounds of the invention as defined herein, which comprise one or more isotopic substitutions. For example, H many be in any isotopic form, including $^1$H, $^2$H(D), and $^3$H(T); C may be in any isotopic form, including $^{12}$C, $^{13}$C, and $^{14}$C; and O may be in any isotopic form, including $^{16}$O and $^{18}$O; and the like.

It is also to be understood that certain compounds of the invention may exist in solvated as well as unsolvated forms such as, for example, hydrated forms. It is to be understood that the invention encompasses all such solvated forms that possess Mps1 kinase inhibitory activity.

It is also to be understood that certain compounds of the invention may exhibit polymorphism, and that the invention encompasses all such forms that possess Mps1 kinase inhibitory activity.

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, $4^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

In a particular aspect, the present invention provides a method of synthesising a compound of the formula I, or a pharmaceutically acceptable salt or solvate thereof, the method comprising:
a) reacting an intermediate of formula A:

Formula A wherein LG is a suitable leaving group;
with an intermediate of formula B:

Formula B wherein x is N or CH; and
b) optionally thereafter, and if necessary, forming a pharmaceutically acceptable salt or solvate thereof.

LG may be any suitable leaving group. In an embodiment, LG is a halogen or any other suitable leaving group (e.g. trifluoromethylsulphonate etc.). In a further embodiment, LG is chloro or bromo.

Any suitable solvent or solvent mixture may be used for this reaction. A person skilled in the art will know how to select suitable solvents or solvent mixtures for use in these reactions. An example of a suitable solvent is dioxane or DMA.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 40 to 120° C. or, more suitably 60 to 100° C., for a suitable time period of, for example, 2 hours to 7 days, or more suitably 2 to 10 hours.

Suitably the reaction takes place in the presence of a suitable catalyst, for example a palladium-derived catalyst (e.g. $Pd_2(dba)_3$).

Suitably the coupling reaction takes place in the presence of an organophosphorus compound, suitably an organophosphorus compound which serves as a suitable ligand to the catalyst. The organophosphorus compound may suitably be a phosphine-derivative, such as Xantphos.

Suitably the coupling reaction takes place in the presence of a base, for example a metal carbonate, such as cesium carbonate.

The resultant compound of formula I can be isolated and purified using techniques well known in the art.

The process defined herein may further comprise the step of subjecting the compound of formula I to a salt exchange, particularly in situations where the compound of formula I is formed as a mixture of different salt forms. The salt exchange suitably comprises immobilising the compound of formula I on a suitable solid support or resin, and eluting the compounds with an appropriate acid to yield a single salt of the compound of formula I.

The compound of Formula A can be prepared by processes known in the art, for example, by the processes defined in International Patent Publication WO2012/123745.

The intermediate of Formula B can be prepared by processes known in the art, suitably by processes described herein with reference to the examples.

In a further aspect of the invention, there is provided a compound of formula I obtainable by a process as defined herein.

In a further aspect of the invention, there is provided a compound of formula I obtained by process as defined herein.

In a further aspect of the invention, there is provided a compound of formula I directly obtained by process as defined herein.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In one aspect, the present invention provides a compound of the invention, or a pharmaceutically acceptable salt or solvate thereof, or a pharmaceutical composition as defined herein for use in therapy.

The compounds of the invention are capable of inhibiting Mps1 kinase activity. Thus, in another aspect, the present invention provides a method of inhibiting Mps1 kinase activity in a cell, the method comprising administering to said cell a compound of the invention as defined herein, or a pharmaceutically acceptable salt or solvate thereof.

In a further aspect, the present invention provides a method of inhibiting Mps1 kinase in vitro or in vivo, said method comprising contacting a cell with an effective amount of a compound of the invention, or a pharmaceutically acceptable salt or solvate thereof, as defined herein.

In another aspect, the present invention provides a method of inhibiting Mps1 kinase activity in a human or animal subject in need of such inhibition, the method comprising administering to said subject an effective amount of a compound of the invention as defined herein, or a pharmaceutically acceptable salt or solvate thereof.

In another aspect, the present invention provides a compound of the invention as defined herein, or a pharmaceutically acceptable salt or solvate thereof for use in the treatment of disease or condition associated with Mps1 kinase activity.

In another aspect, the present invention provides the use of a compound of the invention as defined herein, or a pharmaceutically acceptable salt or solvate thereof, in the manufacture of a medicament for use in the treatment of disease or condition associated with Mps1 kinase activity.

In yet another aspect, the present invention provides a method of treating a proliferative disorder in a human or animal subject, the method comprising administering to said subject a therapeutically acceptable amount of a compound of the invention as defined herein, or a pharmaceutically acceptable salt or solvate thereof.

In yet another aspect, the present invention provides a compound of the invention as defined herein, or a pharmaceutically acceptable salt or solvate thereof, for use in the treatment of a proliferative disorder.

In yet another aspect, the present invention provides the use of a compound of the invention as defined herein, or a pharmaceutically acceptable salt or solvate thereof, in the manufacture of a medicament for use in the treatment of a proliferative disorder.

The term "proliferative disorder" is used herein to refer to an unwanted or uncontrolled cellular proliferation of excessive or abnormal cells which is undesired, such as, neoplastic or hyperplasticgrowth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers by virtue of their Mps1 kinase inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Therefore, in another aspect, the present invention provides a compound of the invention, or a pharmaceutically acceptable salt or solvate thereof, or a pharmaceutical composition as defined herein, for use in the treatment of cancer.

In yet another aspect, the present invention provides the use of a compound of the invention, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound of the invention, or a pharmaceutically acceptable salt or solvate thereof, or a pharmaceutical composition as defined herein.

Examples of particularly suitable cancers that can be treated by the compounds of the present invention include breast cancer (e.g. triple negative breast cancer), lung cancer (e.g. non small cell lung cancer), ovarian cancer (e.g high serous ovarian cancer), AIDS-related Kaposi's Sarcoma, colorectal cancer, pancreatic cancer, head and neck cancer, gastric cancer, and prostate cancer (e.g. metastatic, androgen-independent prostate cancer). In a particular embodiment, the cancer is selected from breast cancer (e.g. triple negative breast cancer), lung cancer (e.g. non small cell lung cancer) or ovarian cancer (e.g high serous ovarian cancer).

In a particular embodiment, the compounds of the invention are used to treat breast cancer, e.g. triple negative breast cancer, optionally in combination with another anti-tumour agent as described herein, e.g. paclitaxel, paclitaxel albumin-stabilized nanoparticle formulation (e.g. Abraxane®) or docetaxel.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel, paclitaxel albumin-stabilized nanoparticle formulation (e.g. Abraxane®) or docetaxel, and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;
(vii) an endothelin receptor antagonist, for example zibotentan (ZD4054) or atrasentan;
(viii) antisense therapies, for example those which are directed to the targets listed above, such as ISIS 2503, an anti-ras antisense;
(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and
(x) immunotherapy approaches, including for example: immune checkpoint blockers, such as PDL-1 and CTLA-4; ex-vivo and in-vivo approaches to increase the immunogenicity of patient tumour cells, such as transfection with cytokines such as interleukin 2, interleukin 4 or granulocyte-macrophage colony stimulating factor; approaches to decrease T-cell anergy, approaches using transfected immune cells such as cytokine-transfected dendritic cells, approaches using cytokine-transfected tumour cell lines and approaches using anti-idiotypic antibodies; and T cell co-stimulatory approaches, such as OX40 and 4-1BB agonists.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(ix) above.

In a further aspect of the invention there is provided a compound of the invention or a pharmaceutically acceptable salt or solvate thereof, in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with an anti-tumour agent selected from one or more of those listed under paragraphs (i)-(ix) herein above, in association with a pharmaceutically acceptable diluent or carrier.

In a further aspect, the present invention provides a compound of the invention, or a pharmaceutically acceptable salt or solvate thereof, for use in the treatment of cancer, wherein the compound of the invention is administered in combination with another anti-tumour agent, optionally selected from one or more of those listed under paragraphs (i)-(ix) herein above. Suitably, the cancer is selected from breast cancer (e.g. triple negative breast cancer), lung cancer (e.g. non small cell lung cancer), ovarian cancer (e.g high serous ovarian cancer), AIDS-related Kaposi's Sarcoma, colorectal cancer, pancreatic cancer, head and neck cancer, gastric cancer, and prostate cancer (e.g. metastatic, androgen-independent prostate cancer).

In a particular aspect, the present invention provides a compound of the invention, or a pharmaceutically acceptable salt or solvate thereof, for use in the treatment of cancer wherein the compound is administered in combination with paclitaxel, paclitaxel albumin-stabilized nanoparticle formulation (e.g. Abraxane®) or docetaxel. Suitably, the cancer is selected from breast cancer (e.g. triple negative breast cancer), lung cancer (e.g. non small cell lung cancer), ovarian cancer (e.g high serous ovarian cancer), AIDS-related Kaposi's Sarcoma, colorectal cancer, pancreatic cancer, head and neck cancer, gastric cancer, and prostate cancer (e.g. metastatic, androgen-independent prostate cancer).

EXAMPLES

General Experimental

Commercially available starting materials, reagents and dry solvents were used as supplied.

Flash column chromatography was performed using Merck silica gel 60 (0.025-0.04 mm). Column chromatography was also performed on a FlashMaster personal unit using isolute Flash silica columns or a Biotage SP1 purification system using Merck or Biotage Flash silica cartridges.

Preparative TLC was performed on Analtech or Merck plates. Ion exchange chromatography was performed using acidic Isolute Flash SCX-II columns, Isolute Si-carbonate columns or basic isolute Flash $NH_2$ columns. Preparative HPLC was conducted using a Phenomenex Luna column (5 μm, 250×21.2 mm, C18, Phenomenex, Torrance, USA) using a Gilson GX-281 Liquid Handler system combined with a Gilson 322 HPLC pump (Gilson, Middleton, USA), over a 15 minute gradient elution (Grad15 mins20 mls·m) from 10:90 to 100:0 methanol:water (both modified with 0.1% formic acid) at a flow rate of 20 mL/min. or over a 15 minute gradient elution (Grad15 mins20 ml·m) from 40:60 to 100:0 methanol:water (both modified with 0.1% formic acid) at a flow rate of 20 mL/min.

UV-Vis spectra were acquired at 254 nm on a Gilson 156 UV-Vis detector (Gilson, Middleton, USA). Collection was triggered by UV signal, and collected using a Gilson GX-281 Liquid Handler system (Gilson, Middleton, USA). Raw data was processed using Gilson Trilution Software. $^1$H NMR spectra were recorded on a Bruker Avance-500. Samples were prepared as solutions in a deuterated solvent and referenced to the appropriate internal non-deuterated solvent peak or tetramethylsilane. Chemical shifts were recorded in ppm (δ) downfield of tetramethylsilane.

LC/MS and HRMS analyses were performed on an Agilent 1200 series HPLC and diode array detector coupled to a 6210 time of flight mass spectrometer with dual multimode APCI/ESI source. Analytical separation was carried out at 30° C. either on a Merck Chromolith SpeedROD column (RP-18e, 50×4.6 mm) using a flow rate of 2 mL/min in a 4 minute gradient elution with detection at 254 nm or on a Merck Purospher STAR column (RP-18e, 30×4 mm) using a flow rate of 1.5 mL/min in a 4 minute gradient elution with detection at 254 nm. The mobile phase was a mixture of methanol (solvent A) and water (solvent B) both containing formic acid at 0.1%. Gradient elution was either: 1:9 (A/B) to 9:1 (A/B) over 2.5 min, 9:1 (A/B) for 1 min, and then reversion back to 1:9 (A/B) over 0.3 min, finally 1:9 (A/B) for 0.2 min (Default method also referred to as ESI-HRMS Method B in the experimental). The following references masses were used for HRMS analysis: caffeine [M+H]$^+$ 195.087652; (hexakis(1H,1H,3H-tetrafluoropentoxy)phosphazene [M+H]$^+$ 922.009798) and hexakis(2,2-difluoroethoxy)phosphazene [M+H]$^+$ 622.02896 or reserpine [M+H]$^+$ 609.280657. LC/MS analysis was also performed on a Waters Alliance 2795 Separations Module and Waters 2487 dual wavelength absorbance detector coupled to a Waters/Micromass LCt time of flight mass spectrometer with ESI source.

Example 1—Synthesis of Isopropyl 6-(2-methoxy-4-(1-methyl-1H-1,2,3-triazol-5-yl)phenylamino)-2-(1-methyl-1H-pyrazol-4-yl)-1H-pyrrolo[3,2-c]pyridine-1-carboxylate Synthesis of 5-(3-Methoxy-4-nitrophenyl)-1-methyl-1H-1,2,3-triazole

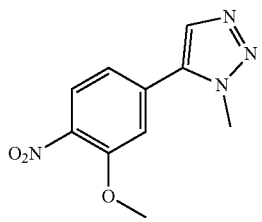 [SMILES: COc1cc(-c2cnnn2C)ccc1[N+](=O)[O-]]

1-Methyl-1H-1,2,3-triazole (41 mg, 0.495 mmol) was dissolved in THF (4.9 mL) and cooled to −78° C. n-Butyllithium solution in hexanes (240 μL, 0.594 mmol) was added dropwise and the solution was stirred for further 5 min before zinc(II) chloride (3.0 mL, 1.485 mmol) was added. After 30 min at −78° C., the reaction mixture was diluted with DMF (2.0 mL), tetrakis(triphenylphosphine)palladium (0) (29 mg, 0.025 mmol) and a solution of 4-bromo-2-methoxy-1-nitrobenzene (115 mg, 0.495 mmol) in DMF (500 μL) were added. The solution was stirred at 80° C. for 2.5 h. After the mixture was cooled to room temperature, water and EtOAc were added and the phases were separated. The organic phase was washed with water, brine, dried (Na$_2$SO$_4$) and the solvent was removed in vacuo. The residue was purified by Biotage silica gel column chromatography eluting with DCM/EtOAc (99/1 to 90/10, 10 g column) to afford the title product as a pale yellow solid (82 mg, 70.7%). $^1$H NMR (500 MHz, CDCl$_3$): δ 4.04 (s, 3H), 4.14 (s, 3H), 7.10-7.13 (m, 2H), 7.82 (s, 1H), 7.98-8.01 (m, 1H); LC (Method B)-MS (ESI, m/z) t$_R$ 1.97 min, 235 [(M+H$^+$), 100%].

Synthesis of 2-Methoxy-4-(1-methyl-1H-1,2,3-triazol-5-yl)aniline

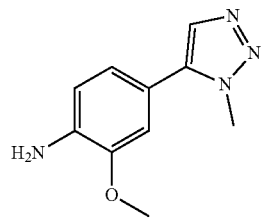

10% Pd on carbon (8 mg, 0.333 mmol) was added to a solution of 5-(3-methoxy-4-nitrophenyl)-1-methyl-1H-1,2,3-triazole (78 mg, 0.333 mmol) in DMF (3.3 μL). The reaction mixture was stirred at 25° C. under a hydrogen atmosphere for 8 h. 8 mg of Pd/C were added and the reaction mixture was stirred overnight. 8 mg of Pd/C were added and the mixture was stirred for 3 days. The reaction mixture was then filtered on SCX-2 column and concentrated under reduced pressure to afford the title product as a white solid (25 mg, 36.8%). $^1$H NMR (500 MHz, CDCl$_3$): δ 3.90 (s, 3H), 4.05 (s, 5H), 6.78-6.80 (m, 2H), 6.84 (dd, J=8.0, 1.8 Hz, 1H), 7.65 (s, 1H); LC (Method B)-MS (ESI, m/z) t$_R$ 1.39 min, 205 [(M+H$^+$), 100%].

Synthesis of Isopropyl 6-(2-methoxy-4-(1-methyl-1H-,2,3-triazol-5-yl)phenylamino)-2-(1-methyl-1H-pyrazol-4-yl)-1H-pyrrolo[3,2-c]pyridine-1-carboxylate

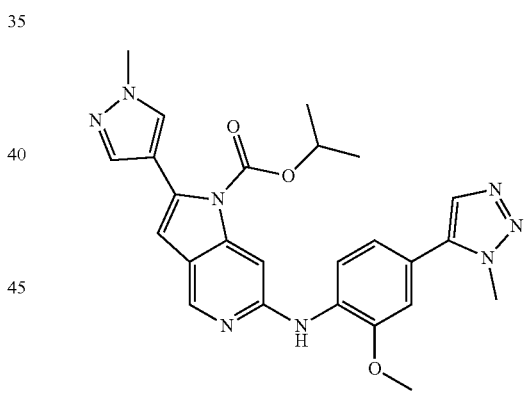

Tris(dibenzylideneacetone)dipalladium(0) (5.7 mg, 6.23 μmol) was added to a mixture of isopropyl 6-bromo-2-(1-methyl-1H-pyrazol-4-yl)-1H-pyrrolo[3,2-c]pyridine-1-carboxylate (45.3 mg, 0.125 mmol; prepared as described in WO2012/123745), cesium carbonate (81 mg, 0.249 mmol), 2-methoxy-4-(1-methyl-1H-1,2,3-triazol-5-yl)aniline (28 mg, 0.137 mmol) and Xantphos (7.2 mg, 0.012 mmol) in DMA (1.4 mL). The reaction mixture was heated at 70° C. for 2 h. It was then filtered on SCX-2 column and concentrated under vacuum. The residue was purified by Biotage column chromatography (0 to 1% MeOH/aq. NH$_3$ (10/1) in EtOAc, 12 g column) and then by preparative TLC (5% MeOH/aq. NH$_3$ (10/1) in DCM) to afford the title product as a white solid (13 mg, 21%). $^1$H NMR (500 MHz, CDCl$_3$): δ 1.34 (d, J=6.3 Hz, 6H), 3.98 (s, 3H), 3.98 (s, 3H), 4.11 (s, 3H), 5.20 (sept, J=6.3 Hz, 1H), 6.54 (d, J=0.9 Hz, 1H), 6.91 (d, J=1.9 Hz, 1H), 7.02 (dd, J=8.3, 1.9 Hz, 1H), 7.57 (s, 1H), 7.63 (s, 1H), 7.71 (s, 1H), 7.75 (t, J=0.9 Hz, 1H), 8.25 (d, J=8.3 Hz, 1H), 8.52 (d, J=0.9 Hz, 1H); $^{13}$C NMR (126 MHz, CDCl$_3$): δ 21.8, 35.5, 39.1, 56.0, 72.1, 96.4, 108.1, 110.3, 114.1, 115.8, 118.2, 121.0, 121.4, 130.2, 132.1, 132.5, 132.6, 138.4, 140.0, 140.5, 144.0, 147.9, 150.9, 151.4; ESI-HRMS (Method B) Found 487.2194, calculated for C$_{25}$H$_{27}$N$_8$O$_3$ (M+H$^+$): 487.2201.

Example 2—Synthesis of Isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate Synthesis of 3-Methoxy-N-methyl-4-nitrobenzamide

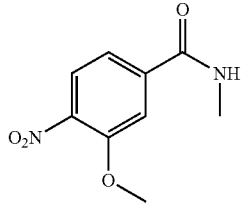

HATU (0.501 g, 1.319 mmol) was added to a solution of 3-methoxy-4-nitrobenzoic acid (0.2 g, 1.014 mmol), DIPEA (0.265 mL, 1.522 mmol) and 2 M methylamine solution in THF (1.0 mL, 2.029 mmol) in THF (2.7 mL). The reaction mixture was stirred at rt overnight. It was then concentrated under reduced pressure and purified by Biotage column chromatography (DCM/EtOAc 80/20 to 60/40; 25 g column) and then (cyclohexane/EtOAc 50/50 to 40/60, 25 g column) to afford the title compound as a white solid (166 mg, 78%). $^1$H NMR (500 MHz, CDCl$_3$): δ 3.07 (d, J=4.9 Hz, 3H), 4.04 (s, 3H), 6.27 (app s, 1H), 7.28 (dd, J=8.3, 1.6 Hz, 1H), 7.64 (d, J=1.6 Hz, 1H), 7.88 (d, J=8.3 Hz, 1H); LC (Method B)-MS (ESI, m/z) t$_R$ 2.04 min, 211 [(M+H$^+$), 100%].

Synthesis of 5-(3-Methoxy-4-nitrophenyl)-1-methyl-1H-tetrazole

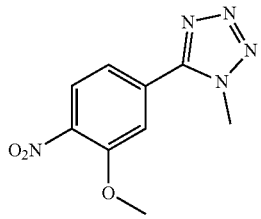 [SMILES: COc1cc(-c2nnnn2C)ccc1[N+](=O)[O-]]

Triflic anhydride (0.27 mL, 1.580 mmol) was added dropwise to a solution of 3-methoxy-N-methyl-4-nitrobenzamide (0.166 g, 0.790 mmol) and sodium azide (0.205 g, 3.16 mmol) in MeCN (4.0 mL) at −10° C. The reaction mixture was warmed up to rt over 3 h. It was then neutralised with sat. aqueous NaHCO$_3$. The mixture was extracted with EtOAc and the organic layer washed with sat. aqueous NaHCO$_3$ and then with brine. It was then dried (Na$_2$SO$_4$) filtered and concentrated under reduced pressure. The residue was then purified by Biotage column chromatography (cyclohexane/EtOAc 70/30 to 50/50, 25 g column) to afford the title compound as a white solid (129 mg, 69%). $^1$H NMR (500 MHz, CDCl$_3$): δ 4.08 (s, 3H), 4.27 (s, 3H), 7.35 (dd, J=8.3, 1.7 Hz, 1H), 7.64 (d, J=1.7 Hz, 1H), 8.04 (d, J=8.3 Hz, 1H); LC (Method B)-MS (ESI, m/z) t$_R$ 1.98 min, 236 [(M+H$^+$), 100%].

Synthesis of 2-Methoxy-4-(1-methyl-1H-tetrazol-5-yl)aniline

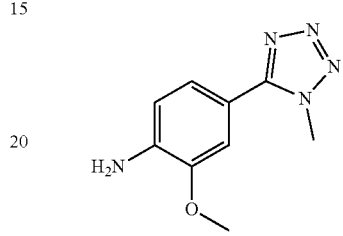

10% Pd on carbon (7 mg, 0.268 mmol) was added to a solution of 5-(3-methoxy-4-nitrophenyl)-1-methyl-1H-tetrazole (63 mg, 0.268 mmol) in EtOAc (1.2 mL). The reaction mixture was stirred at rt under a hydrogen atmosphere for 1 h. Some EtOH (0.5 mL) was added and the reaction mixture was stirred for 1.5 h. It was then filtered and the filtrate was concentrated under reduced pressure to afford the title product as a white solid (52 mg, 95%). $^1$H NMR (500 MHz, CD$_3$OD): δ 3.93 (s, 3H), 4.19 (s, 3H), 6.86-6.88 (m, 1H), 7.20-7.22 (m, 1H), 7.25-7.26 (m, 1H); LC (Method B)-MS (ESI, m/z) t$_R$ 1.54 min, 206 [(M+H$^+$), 100%].

Synthesis of Isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate

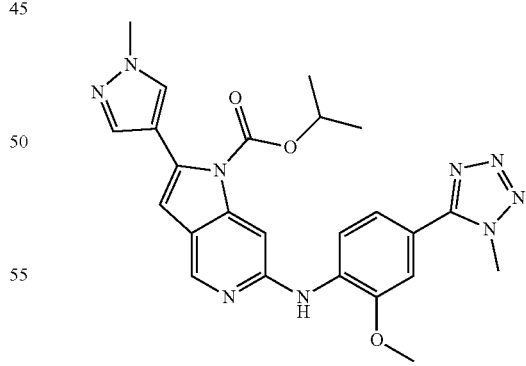

Tris(dibenzylideneacetone)dipalladium(0) (6.3 mg, 6.88 mol) was added to a mixture of isopropyl 6-bromo-2-(1-methyl-1H-pyrazol-4-yl)-1H-pyrrolo[3,2-c]pyridine-1-carboxylate (50 mg, 0.138 mmol; prepared as described in WO2012/123745), cesium carbonate (90 mg, 0.275 mmol), 2-methoxy-4-(1-methyl-1H-tetrazol-5-yl)aniline (31.1 mg, 0.151 mmol) and Xantphos (8.0 mg, 0.014 mmol) in DMA (1.5 mL). The reaction mixture was stirred at 70° C. for 3 h. It was then filtered on SCX-2 column and concentrated under vacuum. The residue was purified by preparative TLC (5% MeOH/aq. NH$_3$ (10/1) in DCM) and then by Biotage column chromatography (DCM/EtOAc, 70/30 to 0/100) to afford the title product as a white solid (34 mg, 51%). $^1$H NMR (500 MHz, CDCl$_3$): δ 1.34 (d, J=6.3 Hz, 6H), 3.98 (s, 3H), 4.02 (s, 3H), 4.21 (s, 3H), 5.20 (sept, J=6.3 Hz, 1H), 6.54 (d, J=0.9 Hz, 1H), 7.26 (dd, J=8.4, 1.9 Hz, 1H), 7.39 (s, 1H), 7.42 (d, J=1.9 Hz, 1H), 7.57 (s, 1H), 7.62 (s, 1H), 7.74 (t, J=0.9 Hz, 1H), 8.39 (d, J=8.4 Hz, 1H), 8.53 (d, J=0.9 Hz, 1H); $^{13}$C NMR (126 MHz, CDCl$_3$): δ 21.8, 35.2, 39.0, 56.1, 72.2, 97.2, 108.1, 110.4, 114.0, 114.3, 114.8, 121.1, 121.3, 130.3, 132.2, 134.4, 140.0, 140.5, 143.9, 147.7, 150.9, 151.0, 154.6; ESI-HRMS (Method B) Found 488.2148, calculated for $C_{24}H_{26}N_9O_3$ (M+H$^+$): 488.2153.

Example 3—Biological Activity

The following biological assays may be used to measure the pharmacological effects of the compounds of the present invention.

Measurement of Inhibition of Mps1 Kinase

The enzyme reaction (total volume 10 µl) was carried out in black 384-well low volume plates containing full length Mps1 (12.5 nM or 3 nM), fluorescent labelled peptide [known as H236, which has the sequence: 5FAM-DHTG-FLTEYVATR-CONH$_2$] (5 µM), ATP (10M), either DMSO (1% v/v) or the test compound (in the range 0.25 nM-100 µM in 1% DMSO) and assay buffer (50 mM HEPES (pH 7.0), 0.02% NaN$_3$, 0.01% BSA, 0.1 mM Orthovandate, 10 µM MgCl$_2$, 1 µM DTT, Roche protease inhibitor). The reaction was carried out for 60 min at room temperature and stopped by the addition of buffer (10 µl) containing 20 mM EDTA, 0.05% (v/v) Brij-35, in 0.1M HEPES-buffered saline (Free acid, Sigma, UK). The plate was read on a Caliper EZ reader II (Caliper Life Sciences).

The reader provides a Software package ('Reviewer') which converts the peak heights into % conversion by measuring both product and substrate peak and also allows selection of control well which represent 0% and 100% inhibition respectively. The % inhibition of the compounds is calculated relative to the means of selected control wells. IC$_{50}$s are determined by testing the compounds at a range of concentrations from 0.25 nM-100 µM. The % inhibitions at each concentration are then fitted to a 4 parameter logistic fit:

$$y=(a+((b-a)/(1+((c/x\widehat{\,}d))))$$

where a=asym min, b=asym max, c=IC$_{50}$ and d=hill coefficient

In the aforementioned Mps1 assay, the compound of Example 1 has an IC$_{50}$ value of 1.2 nM and the compound of Example 2 has an IC$_{50}$ value of 2.8 nM.

MTT Cell Toxicity Assay

Cell proliferation assays were carried out using a colorimetric 3-(4,5-dimethylthiazol-2-yl)-2,5-diphenyltetrazolium bromide (MTT) assay (Sigma). 1.5×10$^3$ HCT116 cells, purchased from ATCC, were plated in 96-well plates at in 100 µL of culture medium in triplicates. Next day three fold dilutions of the compounds to be tested were made in culture medium so that, when diluted, the final concentration in the wells ranged from 0 to 10 µM. 25 µL of compounds dilutions in the medium was added to 100 µL of cells and incubated at 37° C. and 5% CO$_2$ for 72 h. Cells were then incubated with 40 µL of 5 mg/mL MTT reagent at 37° C. for 3 h. The medium was carefully removed and crystals dissolved in 100 µL of DMSO. The absorbance was measured at 570 nm with the Wallac VICTOR2 1420 Multilabel Counter (PerkinElmer) and analysis performed to calculate the GI$_{50}$ using GraphPad PRISM.

Human Liver Microsomal Stability

The human liver microsomal stability of the compounds of the invention was tested using the following procedure:

Mixed gender pooled human liver microsomes were purchased from Tebu-bio (Peterborough, U.K.). Samples contained final concentrations of 1 mg/mL microsomal protein, 3 mmol/L MgCl$_2$, 1 mmol/L NADPH, 2.5 mmol/L, UDP-glucuronic acid, and 10 mmol/L phosphate buffer (pH 7.4) (all purchased from Sigma Aldrich, Gilingham, U.K). Reactions, at 37° C., were started by addition of 10 µmol/L test compound and were terminated at 0, 15 and 30 minutes by the addition of 3 volumes of ice-cold methanol containing internal standard. Samples were centrifuged at 2,800×g for 30 minutes at 4° C. and the supernatants analyzed. Control incubations were prepared as above with omission of cofactors.

The percentage of parent compound remaining at the 30 minute timepoint was recorded.

Pharmacokinetic Profile in Mice ("Mouse PK")

The pharmacokinetic profile of the compounds of the invention was assessed using the following procedure:

Female BALB/c mice (approximately 8 weeks old) from Charles River UK Ltd. (Margate, United Kingdom) were kept in a controlled environment with food and sterilized water available ad libitum. Animals weighed 20±3 g at the time of experiment. Dosing solutions were prepared by dissolving the compounds in 10% DMSO, 5% Tween 20 and 85% saline. The compounds were administered i.v. and p.o. at 5 mg/kg. Animals were warmed before receiving a single i.v. bolus injection into a lateral tail vein. P.o. administration was by gavage. Control animals received the vehicle alone. Groups of three mice were injected per dose route. Blood was collected at 5, 15 and 30 minutes and at 1, 2, 4 and 6 and 24 hours by serial sampling from the tail vein of individual mice after warming using sodium heparin-coated capillaries and 20 µl blood spotted onto Whatman FTA DMPK-B cards. All animal experiments were done in accordance with the Home Office regulations under the Animals (Scientific Procedures) Act 1986 and according to UKCCCR guidelines for animal experimentation.

Calibration standards and QCs were prepared in tail vein blood. 20 µl blood spotted onto Whatman FTA DMPK-B cards. When dry, all standard, QC and sample spots were punched with a Harris Unicore 6 mm punch and 200 µl of methanol containing internal standard was added. Samples were centrifuged for 5 minutes and supernatant taken for analysis by LC-MS. Phoenix WinNonLin (Pharsight) software was used for pharmacokinetic calculations using non-compartmental analysis.

Results

The activity of the compounds of the present invention in comparison with the compounds of Examples 18, 22, 44, 68, 79, 102 and 103 of WO2012/123745 are shown in Table 2 below:

TABLE 2

| Compound | Structure | MTT assay HCT116 GI$_{50}$ (μM) | HLM Assay (% of parent compound degraded at 30 minutes) | Mouse PK Clearance (mL/min/Kg) |
| --- | --- | --- | --- | --- |
| Example 1 | 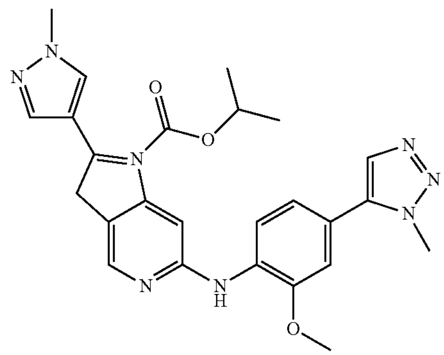 | 0.0594 | 18 | 3.3 |
| Example 2 | 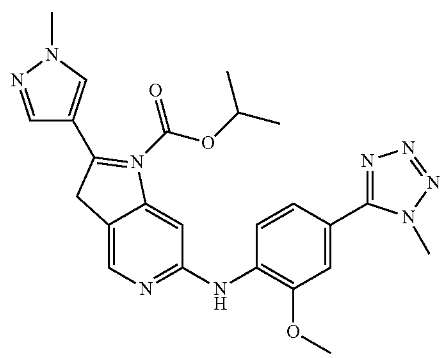 | 0.1043 | 25.1 | 1.5 |
| Comparator 1 Example 18; WO2012/123745 | 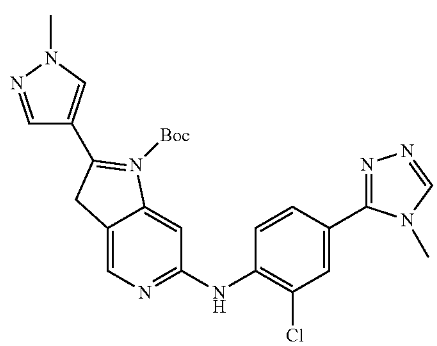 | 0.3595 | 22.1 | 5.0 |
| Comparator 2 Example 22; WO2012/123745 | 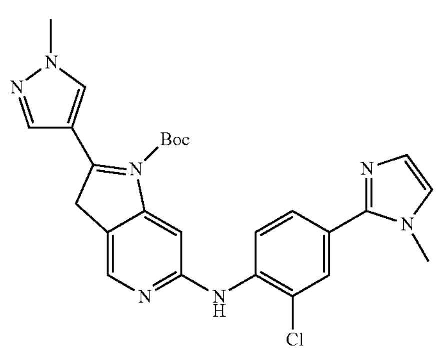 | 0.4135 | 64.1 | |

TABLE 2-continued

| Compound | Structure | MTT assay HCT116 GI$_{50}$ (μM) | HLM Assay (% of parent compound degraded at 30 minutes) | Mouse PK Clearance (mL/min/Kg) |
|---|---|---|---|---|
| Comparator 3 Example 44; WO2012/123745 | 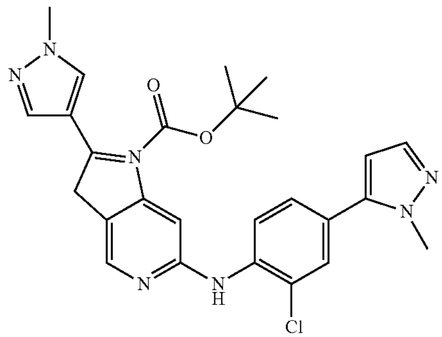 | 0.5477 | 39 | |
| Comparator 4 Example 68; WO2012/123745 | 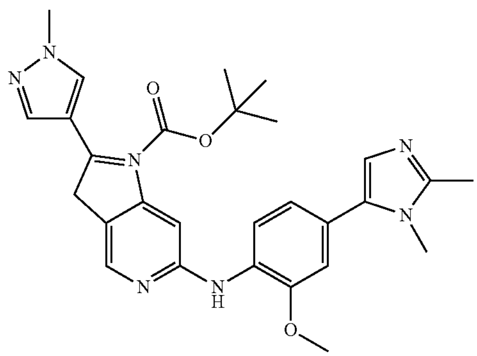 | 0.0912 | 28.9 | 25.0 |
| Comparator 5 Example 79; WO2012/123745 | 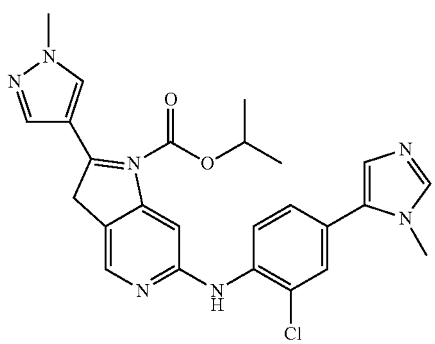 | 0.264 | 86.6 | 15.0 |
| Comparator 6 Example 102; WO2012/123745 | 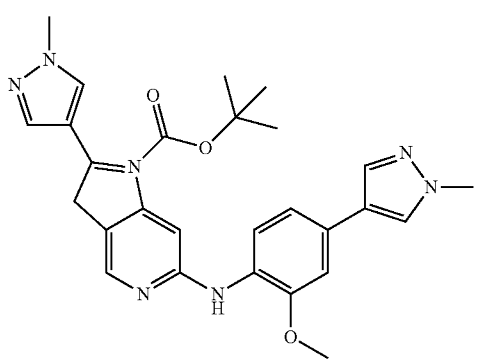 | 0.1481 | 34.7 | 5.0 |

TABLE 2-continued

| Compound | Structure | MTT assay HCT116 GI$_{50}$ (μM) | HLM Assay (% of parent compound degraded at 30 minutes) | Mouse PK Clearance (mL/min/Kg) |
|---|---|---|---|---|
| Comparator 7 Example 103; WO2012/123745 | 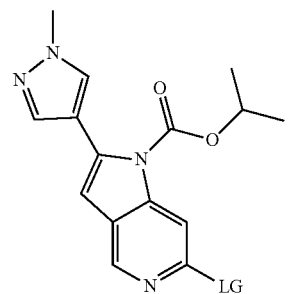 | 0.2336 | 39.7 | 5.0 |

Compounds possessing a GI$_{50}$ in the MTT assay defined herein of 0.15 micromolar or less are preferred, with GI$_{50}$ values of less than 0.11 micromolar being most preferred.

Compounds in which less than 30% of parent compound has degraded at 30 minutes in the HLM assay described herein are preferred, with values of less than 26% being most preferred.

Compounds having clearance values of less than 3.5 mL/min/Kg in the mouse PK studies defined herein are preferred, with values of less than 2 mL/min/Kg being most preferred.

In comparison with the comparator compounds described in WO2012/123745, the compounds of Examples 1 and 2 of the present invention are the only compounds to exhibit a combination of:
1. a GI$_{50}$ in the MTT assay defined herein of 0.15 micromolar or less (or 0.11 micromolar or less);
2. a value of 30% or less (or 26% or less) degradation of the parent compound at 30 minutes in the HLM assay described herein; and
3. a clearance value of less than 3.5 mL/min/Kg in the mouse PK studies defined herein (with the compound of Example 2 of the present invention having a clearance of less than 2 mL/min/Kg).

The invention claimed is:
1. A compound which is one of the following:
isopropyl 6-(2-methoxy-4-(1-methyl-1H-1,2,3-triazol-5-yl)phenylamino)-2-(1-methyl-1H-pyrazol-4-yl)-1H-pyrrolo[3,2-c]pyridine-1-carboxylate; or
isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate;
or a pharmaceutically acceptable salt or solvate thereof.
2. A compound which is:
isopropyl 6-(2-methoxy-4-(1-methyl-1H-1,2,3-triazol-5-yl)phenylamino)-2-(1-methyl-1H-pyrazol-4-yl)-1H-pyrrolo[3,2-c]pyridine-1-carboxylate
or a pharmaceutically acceptable salt or solvate thereof.
3. A compound which is:
isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate
or a pharmaceutically acceptable salt or solvate thereof.

4. A pharmaceutical composition comprising a compound according to claim 1, or a pharmaceutically acceptable salt or solvate thereof, and a pharmaceutically acceptable excipient.

5. A method of treating a proliferative disorder in a patient in need of such treatment, said method comprising administering to said patient a therapeutically effective amount of a compound, or a pharmaceutically acceptable salt or solvate thereof, according to claim 1, wherein the proliferative disorder is breast, ovarian, lung or colon cancer.

6. A method of synthesising a compound according to claim 1, the method comprising:
a) reacting an intermediate of formula A:

Formula A

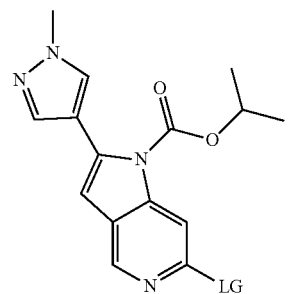

wherein LG is a suitable leaving group;
with an intermediate of formula B:

Formula B

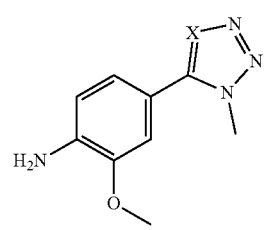

wherein x is N or CH; and
optionally thereafter:
i) removing any protecting groups present; and/or
ii) forming a pharmaceutically acceptable salt or solvate thereof.

7. The method of claim 5, wherein the compound is isopropyl 6-(2-methoxy-4-(1-methyl-1H-1,2,3-triazol-5-yl)phenylamino)-2-(1-methyl-1H-pyrazol-4-yl)-1H-pyrrolo[3,2-c]pyridine-1-carboxylate or a pharmaceutically acceptable salt or solvate thereof.

8. The method of claim 5, wherein the compound is isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate or a pharmaceutically acceptable salt or solvate thereof.

9. The method of claim 6, wherein the compound is isopropyl 6-(2-methoxy-4-(1-methyl-1H-1,2,3-triazol-5-yl)phenylamino)-2-(1-methyl-1H-pyrazol-4-yl)-1H-pyrrolo[3,2-c]pyridine-1-carboxylate or a pharmaceutically acceptable salt or solvate thereof.

10. The method of claim 6, wherein the compound is isopropyl 6-(2-methoxy-4-(1-methyl-1H-tetrazol-5-yl)phenylamino)-2-(1-methyl-1H-pyrazol-4-yl)-1H-pyrrolo[3,2-c]pyridine-1-carboxylate or a pharmaceutically acceptable salt or solvate thereof.

* * * * *